United States Patent
Hansen et al.

(10) Patent No.: US 11,634,835 B2
(45) Date of Patent: Apr. 25, 2023

(54) METHOD FOR SCREENING OF AN IN VITRO DISPLAY LIBRARY WITHIN A CELL

(71) Applicant: VIPERGEN APS, Copenhagen (DK)

(72) Inventors: Nils Jakob Vest Hansen, Copenhagen (DK); Jacob Andersen, Copenhagen (DK); Ole Kristensen, Copenhagen (DK); Allan Beck Christensen, Copenhagen (DK); Lars Kolster Petersen, Copenhagen (DK)

(73) Assignee: VIPERGEN APS, Copenhagen V (DK)

( * ) Notice: Subject to any disclaimer, the term of this patent is extended or adjusted under 35 U.S.C. 154(b) by 0 days.

(21) Appl. No.: 17/424,651

(22) PCT Filed: Jan. 16, 2020

(86) PCT No.: PCT/EP2020/051047
§ 371 (c)(1),
(2) Date: Jul. 21, 2021

(87) PCT Pub. No.: WO2020/152028
PCT Pub. Date: Jul. 30, 2020

(65) Prior Publication Data
US 2022/0090051 A1   Mar. 24, 2022

(30) Foreign Application Priority Data
Jan. 22, 2019 (EP) .................................. 19153025

(51) Int. Cl.
*C40B 30/04* (2006.01)
*C12N 15/10* (2006.01)

(52) U.S. Cl.
CPC .......... *C40B 30/04* (2013.01); *C12N 15/1037* (2013.01); *C12N 15/1068* (2013.01)

(58) Field of Classification Search
None
See application file for complete search history.

(56) References Cited

FOREIGN PATENT DOCUMENTS

| EP | 1423400 B1 | 8/2006 |
| EP | 1402024 B1 | 8/2007 |
| EP | 1809743 B1 | 12/2008 |
| EP | 2622073 B1 | 4/2018 |
| WO | 2000023458 B1 | 4/2000 |
| WO | 2006053571 A2 | 5/2006 |
| WO | 2012041633 A1 | 4/2012 |

OTHER PUBLICATIONS

Petersen et al. (2016) "Novel p38α MAP Kinase Inhibitors Identified from yoctoReactor DNA-encoded Small Molecule Library", Med. Chem. Commun. 7: 1332-1339.
Schurmann et al. (2016) "Small-Molecule Target Engagement in Cells", Cell Chem. Biol. 23:435-441.
(Continued)

*Primary Examiner* — Christian C Boesen
(74) *Attorney, Agent, or Firm* — Agris & von Natzmer, LLP; Cheryl H Agris

(57) ABSTRACT

Provided is a method for screening an in vitro display library for binding within a cell of a small-molecule chemical compound binding entity of the library to a protein or RNA target of interest in order to identify at least one individual chemical compound binding entity of the library that is capable of binding within the cell to the protein or RNA target of interest.

19 Claims, 3 Drawing Sheets
Specification includes a Sequence Listing.

Illustrative example of an embodiment of the method of first aspect herein.

(i): expressing target with a prey in a cell (e.g. oocyte)

(ii): introducing an *in vitro* display library and a bait attached to a nucleic acid molecule (Target DNA – TD) into the cell of (i):

(b): under binding conditions:

(iii+iv): making lysis of the cell of (ii) identifying individual binding entity that binds within the cell to target via:
1. Dilution of supernatant
2. DNA ligation
3. Ligation STOP
4. DNA purification
5. rPCR

(56) References Cited

OTHER PUBLICATIONS

Wu et al. (2015) "Cell-Based Selection Expands the Utility of DNA-Encoded Small-Molecule Library Technology to Cell Surface Drug Targets: Identification of Novel Antagonists of the NK3 Tachykinin Receptor", ACS Comb. Sci. 17: 722-731.
Dudutiene et al. (2014) "Discovery and Characterization of Novel Selective Inhibitors of Carbonic Anhydrase IX", J. Med. Chem. 57: 9435-9446.
Lynn et al. (2014) "Identification of Ligand—Target Pairs from Combined Libraries of Small Molecules and Unpurified Protein Targets in Cell Lysates", J. Am. Chem. Soc. 136: 3264-3270.
Milo (2013) "What is the Total Number of Protein Molecules per Cell Volume?", Bioessays 35: 1050-1055.
Clark et al. (2009) "Design, synthesis and selection of DNA-encoded small-molecule libraries", Nature Chem. Biol. 5:647-654.
Miller et al. (2006) "Directed Evolution by in vitro Compartmentalization", Nature Methods. 3(7): 561-570.
Melkko et al. (2004) "Encoded Self-Assembling Chemical Libraries", Nat. Biotechnol. 22(5): 568-574.
Roberts and Szostak (1997) "RNA-peptide Fusions for the in vitro Selection of Peptides and Proteins", Proc. Natl. Acad. Sci. 94(23): 12297-302.
Ellington et al. (1990) "In Vitro Selection of RNA Molecules That Bind Specific Ligands", Nature. 346: 818-822.
Related PCT appln. No. PCT/EP2020/05104 (published as WO2020152028A1), International Preliminary Reporton Patentability (IPRP), dated Jul. 27, 2021).
Related PCT appln. No. PCT/EP2020/05104 (published as WO 2017/001440A1), International Search Report and Written Opinion, dated Jun. 3, 2020.

Figure 1

Illustrative example of an embodiment of the method of first aspect herein.

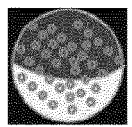

(i): expressing target (POI) in a cell

(ii): introducing an *in vitro* display library into the cell of (i), where:
    (a): the library is a library of at least 1000 different binding entities wherein each binding entity is attached to a nucleic acid molecule:

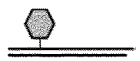

(b): under binding conditions:

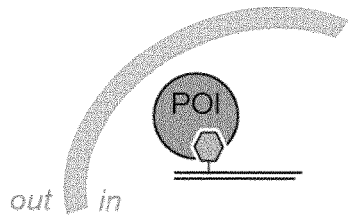

(iii): making lysis of the cell of (ii) to breaking down the membrane of cells in order to:
    (A): get the $B_{BoundTo}T$-structures of (ii) out of the cell:

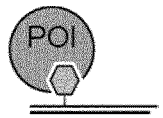

(iv): identifying individual binding entity that binds within the cell to target via binding of target of the $B_{BoundTo}T$-structures to a solid support and remove B-structures not bound to target and use of the specific nucleic acid sequence information allowing to identify the binding entity

Figure 2

Illustrative example of an embodiment of the method of first aspect herein.

(i): expressing target with a prey in a cell (e.g. oocyte)

(ii): introducing an *in vitro* display library and a bait attached to a nucleic acid molecule (Target DNA – TD) into the cell of (i):

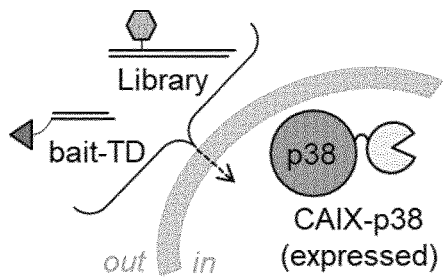

(b): under binding conditions:

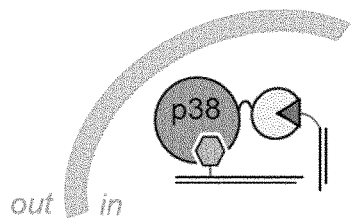

(iii+iv): making lysis of the cell of (ii) identifying individual binding entity that binds within the cell to target via:
1. Dilution of supernatant
2. DNA ligation
3. Ligation STOP
4. DNA purification
5. rPCR

Figure 3
Results of working Example 1 herein – for further details see the Example 1.
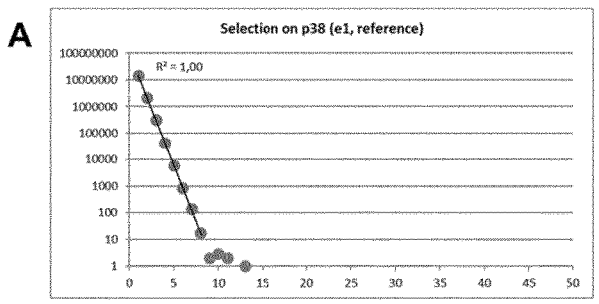
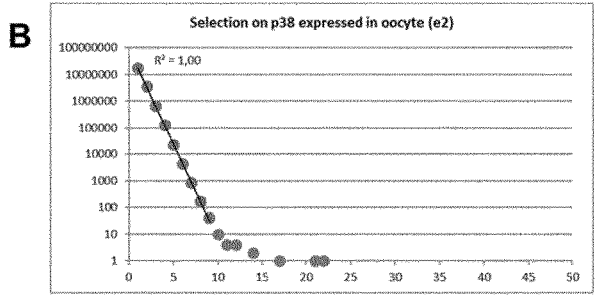
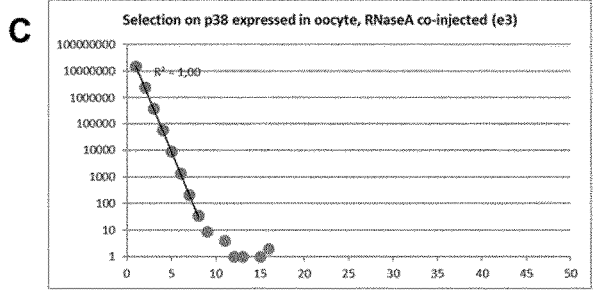
|  | e1 | e2 | e3 |
|---|---|---|---|
| Mathematical threshold (MT) | 9+ | 10+ | 9+ |
| Hit above MT | 8 | 23 | 18 |
| Hit ID# | Cmp ID | #obs (e1) | #obs (e2) | #obs(e3) |
|---|---|---|---|---|
| 1 |  | 13 | - | - |
| 2 |  | 11 | - | - |
| 3 |  | 11 | 8 | 7 |
| 4 |  | 10 | 17 | 15 |
| 5 |  | 10 | 14 | 16 |
| 6 |  | 10 | 5 | - |
| 7 |  | 9 | - | - |
| 8 |  | 9 | 5 | 5 |
| 9 |  | - | 22 | 12 |
| 10 |  | 5 | 21 | 11 |
| 11 |  | - | 14 | 11 |
| 12 |  | - | 12 | - |
| 13 |  | 8 | 12 | 13 |
| 14 |  | 7 | 12 | 16 |
| 15 |  | - | 12 | 11 |
| 16 |  | - | 11 | 8 |
| 17 |  | - | 11 | 5 |
| 18 |  | - | 11 | - |
| 19 |  | - | 11 | - |
| 20 |  | - | 10 | - |
| 21 |  | - | 10 | - |
| 22 |  | - | 10 | - |
| 23 |  | - | 10 | - |
| 24 |  | - | 10 | - |
| 25 |  | - | 10 | - |
| 26 |  | - | 10 | 8 |
| 27 |  | - | 10 | - |
| 28 |  | - | 10 | - |
| 29 |  | - | 10 | - |
| 30 |  | - | 5 | 11 |
| 31 | vpc00249 | - | 5 | 9 |
| 32 |  | - | - | 9 |
| 33 |  | - | 7 | 9 |
| 34 |  | - | - | 9 |
| 35 |  | - | - | 9 |
| 36 |  | - | - | 9 |
| 37 |  | 5 | - | 9 |
| 38 |  | 6 | - | 9 |
| 39 |  | - | - | 9 |

METHOD FOR SCREENING OF AN IN VITRO DISPLAY LIBRARY WITHIN A CELL

FIELD OF THE INVENTION

Provided is a method for screening of an in vitro display library for binding within a cell of a small-molecule chemical compound binding entity of the library to a protein or RNA target of interest in order to identify at least one individual chemical compound binding entity of the library that is capable of binding within the cell to the protein or RNA target of interest.

BACKGROUND

Display technologies have been developed to combine information storage and amplification capabilities of nucleic acids with the functional activities of other compounds. Display technologies rely on an association between a functional binding entity (i.e. phenotype) and a nucleic acid sequence informative (genotype) about the structure of the binding entity. Note: Nucleic acid aptamer technology is considered a display technology although a special case as the pheno- and genotype consist of the same molecule (DNA or RNA).

An advantage of such methods is that very large libraries can be constructed and probed for a desired activity of the functional binding entities. Library members having the desired activity can then be partitioned from library members not having the desired activity, thus creating an enriched library with a higher fraction of members having the desired activity. This process is called selection or enrichment. Some display technologies allow for rounds of selections, where the enriched library from one round is amplified and used to prepare a new enriched display library and used in a next round of selection and so forth. The structures of the library members in the enriched library can then be identified by their cognate nucleic acid sequence, thus allowing identification even from minute amounts of material.

Herein relevant libraries may according to the art be termed "in vitro display libraries".

The term "in vitro display library" shall herein be understood according to the art—i.e. as a library comprising numerous different binding entities wherein each binding entity is attached to a nucleic acid molecule and the nucleic acid molecule comprises specific nucleic acid sequence information allowing to identify the binding entity—i.e. once one knows the specific nucleic acid sequence information of the nucleic acid molecule one directly knows the structure of the specific binding entity attached to the nucleic acid molecule—the structure of the binding entity (i.e. phenotype) attached to the nucleic acid molecule (genotype) is herein termed B-structure.

When the attached nucleic acid molecule is a DNA molecule—the term "in vitro display library" may in the art sometimes be referred to as "DNA-encoded library (DEL)".

The term "binding entity" may in the art sometimes be referred to as "ligand".

The prior art describes a number of different methods to make such in vitro display libraries—herein suitable examples include e.g. EP1809743B1 (Vipergen—YoctoReactor® (yR) library technology), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346 (6287), 818-822 (Ellington), or Proc Natl Acad Sci USA (1997). 94 (23): 12297-302 (Roberts), WO06053571A2 (Rasmussen).

As described in e.g. above-mentioned prior art—one can today make in vitro display libraries comprising very many (e.g. $10^{15}$) specific binding entities (e.g. $10^{15}$ different chemical compounds).

In view of this high number of specific binding entities—it is evident that the selection/enrichment step of such libraries to make an enriched library is important—e.g. to efficient be able to identify the structure of a specific binding entity (e.g. a chemical compound) that binds to a target of interest (e.g. a medical important receptor molecule).

FIG. 3 of EP2622073B1 (Vipergen) shows an example of the in vitro display technology as described in EP1809743B1 (Vipergen—YoctoReactor® (yR) library technology). As can be seen in this FIG. 3 of EP2622073B1, the selection step of this example is performed by immobilizing the target (e.g., a receptor) to a solid surface (e.g., a bead or a glass plate) and non-binders and low affinity binders are typically washed away, whereas the population enriched for binders are recovered from the solid support. Numerous examples of such solid support based selection/enrichment methods are described in the art.

EP2622073B1 (Vipergen) relates as such to an improved in vitro display based method in order to make an enriched library, which is termed Enrichment by Co-Compartmentalization (ECC) or alternatively termed Binder Trap Enrichment® (BTE)—see e.g. FIGS. 1-2 of EP2622073B1 or the Vipergen company home-page: http://www.vipergen.com.

As discussed above, in many prior arts described "in vitro display library" methods, the selection/enrichment step of binding specific binding entity (e.g. a chemical compound) to a target of interest (e.g., a medical important receptor molecule) is performed in a way that may be termed to rely on purified, heterologously expressed proteins in a not natural artificial context—such as e.g., by immobilizing the target (e.g., a receptor) to a solid surface (e.g., a bead or a glass plate).

In relation to binding/selection in such so-called artificial context—the article of Lynn M M et al. ("Identification of Ligand-Target Pairs from Combined Libraries of Small Molecules and Unpurified Protein Targets in Cell Lysates"; J. Am. Chem. Soc. 2014, 136, 3264-3270) reads "the results of selections on immobilized targets may lack biological relevance for proteins that adopt non-native conformations or lack binding partners or cofactors essential for their function when taken out of the cellular context.". In view of this, the article of Lynn describes a so-called interaction determination using unpurified proteins (IDUP) method to identify ligand+target pairs from one-pot mixtures of DNA-linked ligands and unpurified protein targets in cell lysates.

The article of Zining Wu et al. ("Cell-Based Selection Expands the Utility of DNA-Encoded Small-Molecule Library Technology to Cell Surface Drug Targets . . . "; ACS Comb. Sci. 2015, 17, 722-731) describes a cell-based selection method for identifying high affinity and selective ligands against cell surface targets from small-molecule DNA-Encoded Libraries (DELs)—i.e. where the binding is made on cells surfaces, which is not within the cell as such.

The article of M. Schurmann et al. ("Small-Molecule Target Engagement in Cells"; Cell Chemical Biology 23, Apr. 21, 2016) describes that a single specific small-molecule chemical compound may be introduced into a cell and it sometimes may then be possible to identify/detect if this single (one specific) chemical compound binds to a target (e.g., a receptor). As understood by the skilled person in the present context—this M. Schurmann article does not relate to a method for screening an in vitro display library (such as e.g., a DNA-Encoded Library)—i.e., a library comprising numerous (e.g., $10^{10}$) different binding entities. In short, this M. Schurmann article essentially relates to a situation where one already knows that the small-molecule of interest binds to the target (e.g. a receptor) of interest and one essentially simply wants to confirm this within a cell of interest or one wants to study where (e.g. in which compartment of the cell) the binding physically takes place.

In summary and without being limited to theory, the present inventors believe that no prior art document directly and unambiguously describes a method for screening an in vitro display library (e.g. a DNA-Encoded Library (DEL)) for binding within a cell of a small-molecule chemical compound binding entity of the library to a protein or RNA target of interest—i.e. where the library selection/enrichment step of binding specific binding entity (e.g., a chemical compound) to a target of interest (e.g., a medical important receptor molecule) is performed within a cell.

SUMMARY

The problem to be solved by the present invention may be seen as to provide an improved method for screening an in vitro display library for binding of a small-molecule chemical compound of interest to a target of interest (e.g. a medical relevant receptor).

Most previous examples of DNA-encoded library (DEL) screenings are performed on recombinant, purified proteins that are taken out of a cellular context. The purified proteins may lack binding partners or cofactors essential for their function and adopt non-native conformations. Chemical binding entities identified in DEL screenings on purified proteins outside a cellular context may therefore lack biological relevance. In the present invention, DEL screenings are performed on proteins expressed within the cell. Within the cell, the protein of interest can interact with essential binding partners and cofactors in a native environment. Chemical binding entities identified from DEL screenings inside the cell therefore has a higher chance of being biologically active. The latter is particularly important for chemical binding entities which will be applied for drug discovery.

The present invention allows for DEL screenings to be performed on proteins expressed within the cell. The present invention is therefore not dependent on laborious protocols to obtain recombinantly expressed and purified proteins, which are required for most previous examples of DEL screenings.

The working Example (Example 1) describes how the present inventors successfully performed a screening of an in vitro display library (DNA-encoded library) within a cell (i.e. a *Xenopus laevis* oocyte) and identified a number of individual chemical compound binding entities (ligand) of the library that are capable of binding within the cell to the protein target of interest.

As discussed above and without being limited to theory—the present inventors believe that no prior art document directly and unambiguously describes such a "within the cell" method—i.e. where the library selection/enrichment step of binding specific binding entity (e.g. a chemical compound) to a target of interest (e.g. a medical important receptor molecule) is performed in a cell.

Without being limited to theory—it was not prima facie obvious for the present inventors that is was possible to obtain in the working Example herein described "within the cell" very positive screening results—see e.g. the Conclusions of Example 1 herein.

One reason for this relates to that it is known in the art that the "protein density" within a cell is very high, since the cell comprises numerous proteins and other compartments—for instance reads the article of Ron Milo ("What is the total number of protein molecules per cell volume? . . . "; Bioessays 35: 1050-1055, 2013): "we estimate a range of 2-4 million proteins per cubic micron (i.e. 1 fL) in bacteria, yeast, and mammalian cells".

In relation to a method for screening an in vitro display library of the present invention—the high "protein density" within a cell would by the skilled person prima facie be considered a problem, since an in vitro display library comprises numerous (e.g. $10^{10}$) different chemical compound binding entities and it would prima facie be considered not plausible that a substantial amount of "good binders" within the library, actually would be able find the target (e.g. a receptor) of interest and thereby bind the target of interest.

Said in other words, before the disclosure of the present "within the cell" invention—one could prima facie have believed that none (or only very few) of the library chemical compound binding entities would actually be able to find and thereby bind the target (e.g. a receptor) of interest within a cell—i.e. in such a scenario would library binder screening "within the cell" not be technical relevant/useful, since one would not identify a representative amount of good binders compounds of the library.

As discussed herein—by using a "within the cell" library screening method of the present invention, the present inventors identified a number of individual different good binder chemical compound binding entities—i.e. an acceptable representative high number of good binder compounds of the library.

Accordingly, one relevant technical contribution of the present invention may be seen as relating to the fact that the present invention demonstrated that it is actually possible to successfully perform a screening of an in vitro display library (DNA-encoded library) within a cell and thereby identify an acceptable representative high number of individual chemical compound binding entities (ligand) of the library that are capable of binding within the cell to the protein target of interest.

In working Example herein, the cell used was a *Xenopus laevis* oocyte.

However, the "protein density" within a cell possible problem/issue discussed above may be seen as a matter not only relevant for a *Xenopus laevis* oocyte—to the contrary, it may be seen as a general matter of concern for virtually any cell of interest. Accordingly, it is believed that the fact that working Example herein demonstrates that the method of the present invention works for *Xenopus laevis* oocyte makes it plausible that it would also work in a substantial amount of other different cell types (e.g. other eukaryotic cell types such as e.g. a human (e.g. CHO) cell).

Accordingly, a first aspect of the invention relates to a method for screening of an in vitro display library for binding within a cell of a small-molecule chemical compound binding entity of the library to a protein or RNA target of interest in order to identify at least one individual chemical compound binding entity of the library that is capable of binding within the cell to the protein or RNA target of interest and wherein the method comprises the steps of:

(i): expressing at least one target $T_n$, wherein n=1 or more, in a cell and wherein the at least one target is a protein or RNA—the structure of the target is herein termed T-structure;

(ii): introducing an in vitro display library into the cell of (i), wherein:
- (a): the library is a library of at least 1000 different binding entities $B_n$, wherein n=1000 or more, wherein each binding entity is attached to a nucleic acid molecule and the nucleic acid molecule comprises specific nucleic acid sequence information allowing to identify the binding entity—wherein once one knows the specific nucleic acid sequence information of the nucleic acid molecule one directly knows the structure of the specific binding entity attached to the nucleic acid molecule and wherein the binding entities of the library are chemical compounds with an average molecular weight MW below 10000 dalton—the structure of the binding entity attached to the nucleic acid molecule is herein termed B-structure; and
- (b): the library is introduced into the cell under binding conditions, which are conditions where a B-structure containing a binding entity capable of binding to a target molecule, binds more efficiently to the corresponding T-structure, than a B-structure containing a binding entity not capable of binding to the same target do and wherein one within the cell gets binding of at least one of the binding entities to at least one target thereby creating within the cell a complex comprising a B-structure bound to a T-structure, which is termed $B_{BoundTo}$T-structure;

(iii): making lysis of the cell of (ii) to breaking down the membrane of cells in order to:
- (A): get the $B_{BoundTo}$T-structures of (ii) out of the cell and thereby obtain a solution comprising $B_{BoundTo}$T-structures, wherein the $B_{BoundTo}$T-structures are not within the cells; or
- (B): get B-structures out of the cells that had bound to target in step (ii) and have been marked before step (iii) in a way that makes it possible to distinguish the marked B-structures from a B-structure that has not bound to target in step (ii) and thereby obtain a solution comprising binder marked B-structures, wherein the binder marked B-structures are not within the cells; and (iv): identifying, via use of the solution of (iii) and the nucleic acid molecules that comprises the specific nucleic acid sequence information allowing to identify the binding entity of the B-structures, at least one individual binding entity that binds within the cell of (ii) to at least one target of interest.

Step (i) relating to expressing at least one target in a cell may be done according to the art—it is routine work for the skilled person to express a protein or RNA target of interest in a cell of interest. Many times, it may be preferred that the target is a heterologous expressed target.

According to the art—the term "heterologous" relates to a target (e.g. a protein) that is experimentally put into a cell that does not normally make (i.e. expresses) that target (e.g. a protein).

However, in some cases it may be preferred that the target is a target naturally expressed in the cell—e.g. a human receptor target naturally expressed in a human (e.g. CHO) cell. In some cases, it may be preferred that the target is expressed in cells originating from a transgenic host—e.g. a modified version of a human receptor target.

As discussed above, the prior art describes a number of different methods to make an in vitro display library as such—accordingly making the in vitro display library as such of step (ii) may be done according to known prior art techniques for making such in vitro display libraries.

Step (ii) refers to "introducing an in vitro display library into the cell of (i)"—essentially this step may be made based on prior art know techniques.

As discussed in working Example herein—when the cell is a *Xenopus laevis* oocyte may the library be introduced into the oocyte cell via prior art known injection techniques and there is no reason to believe that injection (e.g. microinjection) would not work in a substantial amount of other mammalian cell types.

Alternatively, and depending on the cell type of interest—it may e.g. be done by transfection (e.g. electroporation or chemical based).

It is routine work for the skilled person to identify suitable "binding conditions" according to step (ii)(b).

Essentiality, the "binding conditions" of step (ii)(b) are generally the natural binding conditions within the cell—i.e. one of the advantages of the present invention is that the binding entity (ligand) can bind the target under "binding conditions" of step (ii)(b) that may be natural within the cell binding conditions.

Step (iii) refers to "making lysis of the cell of (ii) to breaking down the membrane of cells"—essentially this step may be made based on known prior art techniques.

Also step (iv) may be made by based on known prior art techniques as e.g., discussed above. In short and as discussed in further detail herein, this "identifying . . . at least one individual binding entity that binds within the cell of (ii) to at least one target of interest" of step (iv) may be made in different ways and based on the common general knowledge and the technical teaching herein, it is routine work for the skilled person to perform this step (iv).

In short, based on the detailed description herein and the common general knowledge—the skilled person may perform all of the individual steps (i) to steps (iv) of the first aspect in a number of different ways/embodiments.

Embodiments of the present invention are described below, by way of examples only.

BRIEF DESCRIPTION OF THE DRAWINGS

FIG. 1: Illustrative example of an embodiment of the method of first aspect (i.e. claim 1) herein.

FIG. 2: Illustrative example of an embodiment of the method of first aspect (i.e. claim 1) herein, where used Prey-Bait FIG. 3: Results of working Example 1 herein—for further details see the Example 1.

DETAILED DESCRIPTION

Step (i) of First Aspect

As discussed above, step (i) reads:

"(i): expressing at least one target $T_n$, wherein n=1 or more, in a cell and wherein the at least one target is a protein or RNA—the structure of the target is herein termed T-structure"

The target may be any suitable protein or RNA target of interest.

As discussed above, it is routine work for the skilled person to express a protein or RNA target of interest in a cell of interest.

As discussed in working Examples herein and as known in the art—when the cell is a *Xenopus laevis* oocyte, the expression of the target may be done by injection of mRNA and it may be preferred.

However, expression of the target in the cell may be done in other well known suitable ways, such as via routine recombinant expression (via e.g. use of an expression vector made of e.g. DNA) of the target of interest in the cell of interest.

Many times, it may be preferred that the target is a heterologous expressed target. According to the art—the term "heterologous" relates to a target (e.g. a protein) that is experimentally put into a cell that does not normally make (i.e. expresses) that target (e.g. a protein).

In some cases, it may be preferred that the target is heterologously expressed in a specific cellular compartment within the cell—e.g. in the nucleus. For the skilled person, this can be done be installing a leader sequence or signal sequence in the target construct.

Preferably, the target is a protein.

As known in the art—a suitable target could e.g. be a receptor molecule present in e.g. the human body and one would be interested in identifying a binding entity (e.g. a chemical compound) that can bind to the receptor.

Accordingly, the target may preferably be a receptor such as e.g. a receptor protein molecule.

In accordance with the prior art—suitable examples may be wherein the target is an autoantigen, a bacterial protein, a blood protein, a cell adhesion protein, a cytokine, a cytoskeleton protein, a DNA-binding protein, a developmental protein, an engineered protein, an enzyme, an extracellular matrix protein, a GTP-binding protein regulator, a glycoprotein, a growth factor, a heat shock protein, a lipoprotein, a membrane protein, a metalloprotein, a motor protein, a phosphoprotein, a prion, a protein complex, a protein domain, a RNA-binding protein, a receptor, a recombinant protein, a seed storage protein, a structural protein, a transcription coregulator protein, a transport protein, a viral protein or fragments hereof.

In short, the skilled person is aware of numerous different possible targets than could be of interest in the present context.

In some cases, it may be preferred to modify the expressed target protein—e.g. by phosphorylation, methylation, acetylation or dephosphorylation. By the skilled person, this can be done by co-expressing a modifying enzyme—e.g. a kinase, methyltransferase, acetyltransferase or a phosphatase—together with the target protein.

As discussed above, it is believed that the fact that the working example herein demonstrates that the method of the present invention works when the cell is a *Xenopus laevis* oocyte makes it plausible that it would also work in a substantial amount of other different cell types (e.g. other eukaryotic cell types such as e.g. a human (e.g. CHO) cell).

Preferably, the cell is a eukaryotic cell such as e.g. mammalian cell, preferably wherein the mammalian cell is a human (e.g. CHO).

In the working example herein is shown that it is possible to introduce (via injection) into one single individual cell (i.e., a *Xenopus laevis* oocyte) an in vitro display library comprising numerous different binding entities.

Accordingly, in a preferred embodiment, the cell is a *Xenopus* oocyte, such as e.g. *Xenopus tropicalis* oocyte or *Xenopus laevis* oocyte—most preferably the cell is a *Xenopus laevis* oocyte.

The term "a cell" of step (i) may be a single cell (e.g. when the cell is a *Xenopus laevis* oocyte).

However, as understood by the skilled person in the present context—the term "a cell" of step (i) may in practice many times refer to a population of cells, wherein individual cells of the population recombinantly express the target of interest.

For instance, wherein the target is expressed by use of e.g. an expression vector in a standard/routine recombinant expression of target in a cell type of interest (e.g. human CHO cells), this will generally give a population of cells, wherein individual cells of the population recombinantly express the target of interest.

Step (i) of first aspect reads "at least one target $T_n$, wherein n=1 or more".

An advantage of the method as described herein is that one in an efficient and rapid way can simultaneously screen for binding entities that could bind to e.g., two or more targets.

For instance, the targets could be two different receptor molecules and the method as described herein could then simultaneously identify one binding entity that binds to one of the receptors and another binding entity that binds to the other receptor.

In the example above (with two different e.g. receptor targets), we would have a situation, wherein the target Tn (n=2) or alternatively expressed $T_2$.

In line with the above, it may be relevant to have at least two different targets in step (i) [i.e. Tn (n=2 or more], or to at least three different targets in step (i) [i.e. Tn (n=3 or more], or to have at least ten different targets in step (i) [i.e. Tn (n=10 or more], or to at least hundred different targets in step (i) [i.e. Tn (n=100 or more].

Without being limited to theory it may be difficult to have more than 1000 different targets in step (i)—i.e. more than 1000 different T-structures in the cell.

Step (ii) of First Aspect

As discussed above, step (ii) relates to:

"(ii): introducing an in vitro display library into the cell of (i), wherein:
  (a): the library is a library of at least 1000 different binding entities $B_n$, . . . and wherein the binding entities of the library are chemical compounds with an average molecular weight MW below 10000 dalton; and
  (b): the library is introduced into the cell under binding conditions, . . . "

Step (ii) refers to "introducing an in vitro display library into the cell of (i)"—essentially this step may be made based on prior art know techniques.

As discussed in the working Example herein, when the cell is a *Xenopus laevis* oocyte, the library may be introduced into the oocyte cell via known prior art injection techniques and there is no reason to believe that injection (e.g. micro-injection) would not work in a substantial amount of other mammalian cell types. Alternatively, and depending on the cell type of interest—it may e.g. be done by transfection (e.g. electroporation or chemical based).

In the working Example herein, it is shown that it is possible to introduce (via injection) into one single individual cell (i.e. a *Xenopus laevis* oocyte) an in vitro display library comprising numerous (approx. $10^8$) different binding entities.

The term "the cell" of step (ii) may be a single cell (e.g. when the cell is a *Xenopus laevis* oocyte).

However, as discussed above, the term "a cell" of step (i) may in practice many times refer to a population of cells and in such a case term "the cell" of step (ii) may in practice be the population of cells of step (i).

As understood by the skilled person in the present context, f one in step (ii) e.g. introduces an in vitro display library of e.g., $10^6$ different binding entities into population of cells of step (i) (e.g. human CHO with recombinantly expressed target) by e.g., transfection then there may be introduced different numbers of binding entities into each cell of the population—such as e.g., some cells of the population may comprise less than 5 binding entities (e.g., one binding entity) and other cells of the population may comprises more than 1000 different binding entities.

The term "in vitro display library" shall be understood according to the art—i.e. as a library comprising numerous different binding entities wherein each binding entity is attached to a nucleic acid molecule and the nucleic acid molecule comprises specific nucleic acid sequence information allowing to identify the binding entity—i.e. once one knows the specific nucleic acid sequence information of the nucleic acid molecule one directly knows the structure of the specific binding entity attached to the nucleic acid molecule—the structure of the binding entity (i.e. phenotype) attached to the nucleic acid molecule (genotype) is herein termed B-structure.

When the attached nucleic acid molecule is a DNA molecule—the term "in vitro display library" may in the art sometimes be referred to as "DNA-encoded library (DEL)".

The term "binding entity" may in the art sometimes be referred to as "ligand".

As discussed herein—the prior art describes a number of different methods to make such in vitro display libraries—i.e. an in vitro display library of step (i).

Said in other words, it is today routine work for the skilled person to properly make a structure of the binding entity (i.e. phenotype) attached to the nucleic acid molecule (genotype)—i.e. what is herein termed a "B-structure".

As known in the art, the binding entity (i.e. phenotype) may be attached to the nucleic acid molecule (genotype) by e.g. a covalent binding or e.g. a high affinity non-covalent binding.

It may herein be preferred that the binding entity (i.e. phenotype) is attached to the nucleic acid molecule (genotype) by a covalent binding.

An in vitro display library of step (i) comprises a number of different B-structures—i.e. in line of above it is routine work for the skilled person to make an in vitro display library of step (i).

Herein suitable examples include e.g. EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts).

Said in other words, the in vitro display library of step (i) of first aspect may be made in a number of ways as described in the prior art.

Without being limited to theory, herein suitable examples of in vitro display library technologies include DNA Encoded Chemical Library technologies, Aptamer technologies, RNA/DNA display technologies such as CIS display, Ribosome display, mRNA display or bead display system (using nucleic acids for encoding).

As described in the prior art (see e.g. EP1809743B1 (Vipergen))—the nucleic acid molecule of the B-structure may e.g. be PNA, LNA, RNA, DNA or combinations thereof. Preferably, the nucleic acid molecule of the B-structure is DNA.

In a preferred embodiment of the present invention, the nucleic acid molecule (genotype) attached to the binding entity (phenotype) in the B-structure may be a double stranded nucleic acid molecule.

In a preferred embodiment of the present invention, the nucleic acid molecule (genotype) attached to the binding entity (phenotype) in the B-structure may be at least 0% double stranded (i.e. single stranded), may be at least 10% double stranded, at least 20% double stranded, at least 30% double stranded, at least 40% double stranded, at least 50% double stranded, at least 60% double stranded, at least 70% double stranded, at least 80% double stranded, at least 90% double stranded, or 100% double stranded.

In a preferred embodiment of the present invention, the nucleic acid molecule (genotype) attached to the binding entity (phenotype) in the B-structure may contain a PCR priming site or a fraction hereof.

In a preferred embodiment of the present invention, the nucleic acid molecule (genotype) attached to the binding entity (phenotype) in the B-structure may contain 2 PCR priming sites or fractions hereof.

In a preferred embodiment of the present invention, the nucleic acid molecule (genotype) attached to the binding entity (phenotype) in the B-structure may contain at least 3 PCR priming sites or fractions hereof.

In some embodiments of the present invention, a fraction of a PCR priming site comprises at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In some embodiments of the present invention, the nucleic acid molecule (genotype) attached to the binding entity (phenotype) in the B-structure may contain a single stranded overhang reverse complement to a single stranded overhang of another relevant nucleic acid molecule (genotype) used in the method as described herein (e.g. a nucleic acid molecule attached to a bait as discussed below). The overhang may preferentially be 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides long.

The binding entity may be any suitable binding entity of interest, wherein the binding entities of the library are chemical compounds with an average molecular weight MW below 10000 dalton, more preferably an average molecular weight MW below 5000 dalton, even more preferably an average molecular weight MW below 1000 dalton.

Suitable examples of a herein relevant chemical compound binding entity may be found in the prior art—see e.g. EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts).

In short, the skilled person is aware of numerous different possible binding entities that could be of interest in the present context.

Step (ii) of first aspect reads "at least 1000 different binding entities $B_n$, wherein n=1000 or more".

In practice, there may many times be many more different binding entities present in the library of step (i)—such as e.g. at least $10^4$, at least $10^6$ or at least $10^8$ different binding entities—i.e. where n=at least $10^4$, n=at least $10^6$ or n=at least $10^8$.

In working Examples herein is shown that it is possible to introduce (via injection) into one single individual cell (i.e. a *Xenopus laevis* oocyte) an in vitro display library comprising numerous (approx. $10^8$) different binding entities.

Accordingly, in a theoretical situation, wherein the library comprises exactly $10^4$ different binding entities—one may herein express this as $B_n$ (n=$10^4$) or $B_{10}{}^4$.

Without being limited to theory it may be difficult to make a library with more than $10^{20}$ different binding entities.

Step (ii)(b) reads:

"(b): the library is introduced into the cell under binding conditions, which are conditions where a B-structure containing a binding entity capable of binding to a target molecule, binds more efficiently to the corresponding T-structure, than a B-structure containing a binding entity not capable of binding to the same target do and wherein one within the cell gets binding of at least one of the binding entities to at least one target thereby creating within the cell a complex comprising a B-structure bound to a T-structure, which is termed $B_{BoundTo}$T-structure"

The term "binds more efficiently" shall be understood according to common practice e.g. higher affinity, faster on rate, or slower dissociation rate.

As known to the skilled person—in the present context it is routine work for the skilled person to perform step (ii)(b) under conditions, wherein one get this "binds more efficiently" effect.

It would be routine work for the skilled person to optimize the binding conditions of step (ii)(b) in order to get the required "binds more efficiently" effect of step (ii)(b).

As discussed above, the "binding conditions" of step (ii)(b) are generally the natural binding conditions within the cell—i.e. one of the advantages of the present invention is that the binding entity (ligand) can bind the target under "binding conditions" of step (ii)(b) that may be natural within the cell binding conditions.

As known to the skilled person—herein relevant optimization parameters may e.g., be ionic strength, temperature etc.

Accordingly, under any practical herein relevant circumstance—the skilled person would not be in any reasonable doubt if he (after e.g. proper routine adjustment of the binding conditions) would work under binding conditions of step (ii)(b) or not.

In a preferred embodiment, step (ii)(b) is performed under binding conditions, wherein a B-structure containing a binding entity capable of binding to a target molecule, binds 10 fold (more preferably 100 fold, even more preferably 1000 fold) more efficiently to the corresponding T-structure, than a B-structure containing a binding entity not capable of binding to the same target do.

The method as described herein allows optimizing of major binding characteristics for binding of binding entity to target, for example, potency (affinity), association rate (on rate) or dissociative half-life of binding entity and target (off rate).

Affinity based selection is achieved in binding step (ii)(b) e.g. by using equilibrium conditions and controlled by the target concentration in the binding step—for instance, binding conditions wherein 90% of the molecules of a binding entity in the display library having a $K_d$ equal to 10 times smaller than the target concentration are target bound or binding conditions wherein 90% of the molecules of a binding entity in the display library having a $K_d$ equal to 2 times smaller than the target concentration are target bound.

In a preferred embodiment of the present invention—the concentration of T-structures in the "binding step step (ii) (b)" is at least $10^{-15}$ M, at least $10^{-14}$ M, at least $10^{-13}$ M, at least $10^{-12}$ M, at least $10^{-11}$ M, at least $10^{-10}$ M, at least $10^{-9}$ M, at least $10^{-8}$ M, at least $10^{-7}$ M, at least $10^{-6}$ M, at least $10^{-5}$ M, or at least $10^{-4}$ M. In the working example herein (see below) the concentration of T-structures in the "binding step" step (ii)(b) was around $200 \times 10^{-9}$ M.

Alternatively, association rate based selection is achieved by controlling the time allowed for the binding step step (ii)(b)—accordingly, the "binding step" may be performed for a time period shorter than the time needed to reach binding equilibrium conditions.

Step (iii) of First Aspect

As discussed above, step (iii) reads:

"(iii): making lysis of the cell of (ii) to breaking down the membrane of cells in order to:
(A): get the $B_{BoundTo}$T-structures of (ii) out of the cell and thereby obtain a solution comprising $B_{BoundTo}$T-structures, wherein the $B_{BoundTo}$T-structures are not within the cells; or
(B): get B-structures out of the cells that had bound to target in step (ii) and have been marked before step (iii) in a way that makes it possible to distinguish the marked B-structures from a B-structure that has not bound to target in step (ii) and thereby obtain a solution comprising binder marked B-structures, wherein the binder marked B-structures are not within the cells"

Step (iii) refers to "making lysis of the cell of (ii) to breaking down the membrane of cells"—essentially this step may be made based on prior art know techniques such as e.g. by mechanical crushing (e.g. centrifugation or pipetting) or by chemical lysis (e.g. by use of SDS to dissolve the membrane).

In view of the common general knowledge of the skilled person and the technical teaching herein (see e.g. below)—the skilled person may perform step (iii) in numerous different suitable ways.

As understood by the skilled person and discussed herein—whether one uses option step (iii)(A) or step (iii)(B) may be seen as relating to how one prefers to make the identifying step (iv).

It may be preferred that step (iii) is step (iii)(A).

As illustrated in FIG. 1 herein—in a situation wherein step (iii) is step (iii)(A) it may e.g. be that step (iv) is done by:

binding $B_{BoundTo}$T-structures of the solution (iii)(A) of to a solid support via binding of target of the $B_{BoundTo}$T-structures to the solid support and remove B-structures not bound to target and thereby not bound to the solid support; and identifying, via use of the specific nucleic acid sequence information allowing to identify the binding entity of the $B_{BoundTo}$T-structures bound to the solid support, at least one individual binding entity that binds within the cell of (ii) to at least one target of interest.

As illustrated in FIG. 2 herein and in the working example herein, n a situation wherein step (iii) is step (iii)(A), the method as described herein may preferably be done by a method wherein:

the T-structure of (i) of the first aspect comprises a prey (e.g. a target-prey fusion protein) and there in step (ii) of the first aspect is also introduced a bait attached to a nucleic acid molecule (which e.g. has complementary cohesive ends to the nucleic acid molecule of the B-structure) and the nucleic acid molecule comprises specific nucleic acid sequence information allowing to identify the specific target and wherein the bait binds to the prey of the target in step (ii) and thereby creates $B_{BoundTo}$T-structures with the bait bound to the prey of target;

after lysis step (iii)(A)—fusing (e.g. by ligating via use of a ligase) the nucleic acid molecules of the $B_{BoundTo}$T-structures with the bait bound to the prey of target, wherein the fused nucleic acid molecules comprise the sequence information allowing to identify binding entity and target; and identifying in step (iv) via use of the specific nucleic acid sequence information allowing to identify the binding entity and target of the fused (e.g. ligated) nucleic acid molecules of the preceding step at least one individual binding entity that binds within the cell of (ii) to at least one target of interest.

Before the "fusing (e.g. by ligating via use of a ligase) the nucleic acid molecules of the $B_{BoundTo}$T-structures with the bait bound to the prey of target" step it may be preferred to make a dilution step (e.g. a dilution step of the solution (e.g. supernatant) obtained from cell lysis step (iii). It may be preferred that the dilution step of the solution (e.g., supernatant) obtained from cell lysis step (iii) (preferably step (iii)(A)) is a diluting the solution of at least $10^2$ fold, such as at least $10^3$ fold, at least $10^4$ fold, or at least $10^5$ fold. In the working example herein (see below), the dilution of the solution was around $10^4$ fold. An advantage of this diluting step is that not bound B and T-structures (i.e. B and T-structures alone as such) may after dilution be even further physically apart from each other in the solution and there will then less "false positives" after the "fusing the nucleic acid molecules of the $B_{BoundTo}$T-structures" step.

After the "fusing (e.g. by ligating via use of a ligase) the nucleic acid molecules of the $B_{BoundTo}$T-structures with the bait bound to the prey of target" step it may be preferred to make a purification of the fused (e.g. ligated) nucleic acid molecules—e.g. in order to have more pure nucleic acid molecules (e.g. DNA) for e.g. a subsequent amplification (e.g. via PCR) step. The skilled person in the art can routinely identify numerous different strategies in order to purify nucleic acid molecules (e.g., DNA) of interest, without being limited for example by agarose gel electrophoresis, polyacrylamide gel electrophoresis, spin-columns, etc.

The "identifying" step (iv) preferably comprises a step, wherein the fused nucleic acid molecules that comprise the sequence information for binding entity and for target are amplified (preferably by use of polymerase chain reaction (PCR)).

As evident, if there is only one target (i.e. n=1 in step (i), then is the identifying of at least one individual binding entity essentially done by use of the specific nucleic acid sequence information allowing to identify the binding entity.

The prior art within the herein relevant field of biotechnology describes numerous herein suitable "prey-bait" systems, such as e.g.:
prey: tetrameric streptavidin and bait: biotin;
prey: monomeric streptavidin (e.g. mSA2) and bait: biotin;
prey: His-tag and bait: NTA;
prey: SNAP-tag® and bait: benzyl guanin (BG);
prey: Halo-Tag® and bait: reactive chloroalkane linker bound to a functional group;
prey: carbonic anhydrase IX (CAIX) and bait: VD11-4-2; or
prey: maltose binding protein (MBP) and bait: maltose or malt triose.

In the working example herein is the "prey-bait" system—prey: carbonic anhydrase IX (CAIX) and bait: VD11-4-2—accordingly, this is preferred "prey-bait" system.

The "prey-bait" system—prey: carbonic anhydrase IX (CAIX) and bait: VD11-4-2 is described in e.g. the article of V. Dudutiene et al. ("Discovery and Characterization of Novel Selective Inhibitors of Carbonic Anhydrase IX"; J. Med. Chem. 2014, 57, 9435-9446), where it is described that VD11-4-2 is the small chemical compound with the structure:

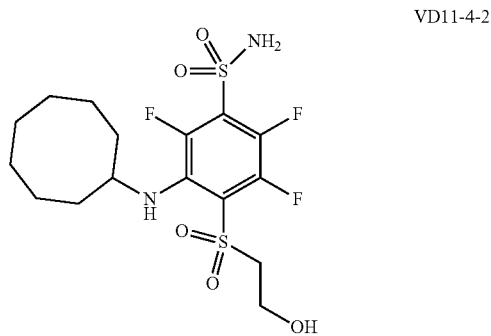 [SMILES: NS(=O)(=O)c1c(F)c(F)c(S(=O)(=O)CCO)c(NC2CCCCCCC2)c1F]

VD11-4-2

Preferably, the T-structure of (i) of the first aspect that comprises a prey is obtained by expressing a target-prey fusion protein (e.g. target-CAIX) within the cell—see e.g. working Example herein for an example of this.

It is routine work for the skilled person to express a target-prey fusion protein within a cell of interest.

A possible embodiment could be where the bait actually binds to binding site of target, which is different to binding site of binding entity (i.e. ligand).

In the present context "fusing (e.g. by ligating) the nucleic acid molecules of the $B_{BoundTo}$T-structures with the bait bound to the prey of target" shall be understood as joining the genetic information carried by the two genotypes (i.e. nucleic acid molecule with sequence information for binding entity and nucleic acid molecule with sequence information for target).

As known to the skilled person (see e.g. [0166] of EP2622073B1 (Vipergen)), this "fusing" can be accomplished in several ways such as e.g.:
a) information transfer by e.g. overlap PCR or overlap genome extension;
b) information joining catalyzed by an enzyme forming an amplifiable facilitating bond—e.g., by a DNA ligase where a phosphodiester bond between at least one of the strands from each nucleic acid molecule is formed. Preferably, the fusing is done by ligating via use of a ligase. If a e.g., a ligase enzyme is used to get the fusing of nucleic acid molecules—then one does not need to have any base pairing overlapping regions between the nucleic acid molecules.

However, it may be preferred (independently if e.g., ligase is used or not) that the nucleic acid molecule attached to the bait is a nucleic acid molecule, which has complementary cohesive ends to the nucleic acid molecule of the B-structure—more preferably, wherein there are phosphorothioate bonds at the complementary cohesive ends of the nucleic acid molecules of both the nucleic acid molecule of the B-structure and the nucleic acid molecule attached to the bait.

Preferably, there are phosphorothioate bonds installed in the phosphate backbone at the complementary cohesive ends of the nucleic acid molecule of the B-structure and the nucleic acid molecule attached to the bait. The number of phosphorothioate bonds may for each nucleic acid molecule preferentially be at least 1 phosphorothioate bond, at least 2 phosphorothioate bonds or more preferably at least 3 phosphorothioate bonds. In the working example, Example 1, 3 phosphorothioate bonds were used and the results of Comparative Example 2 herein demonstrate that use of 3 phosphorothioate bonds gives surprising significant technically advantages in the present context as compared to use of unmodified DNA (i.e. zero phosphorothiate bonds).

In some cases, it may be preferred that the number of phosphorothioate bonds may for each nucleic acid molecule preferentially be at least 4 phosphorothioate bonds, such as at least 10 phosphorothioate bonds or at least 20 phosphorothioate bonds.

Similar to the B-structure—the nucleic acid molecule attached to the bait is e.g. PNA, LNA, RNA, DNA or combinations thereof—preferably, the nucleic acid molecule is DNA.

Other preferred embodiments for the nucleic acid molecule of the B-structure as discussed above (e.g. may be a double stranded nucleic acid molecule; may contain a PCR priming site; etc.) may also be preferred embodiments for the nucleic acid molecule attached to the bait.

The "fusing (e.g. by ligating) the nucleic acid molecules" may be done wherein there is a significant binding of the binding entities to target of the $B_{BoundTo}$T-structures—an example of this is illustrated in FIG. 2 herein and working example herein.

However, as discussed in e.g. EP2622073B1 (Vipergen)—the "fusing (e.g. by ligating) the nucleic acid molecules" may be done wherein there is essentially no binding of the binding entities to target of the $B_{BoundTo}$T-structures—i.e. this is also a possible option in relation to the method as described herein.

Accordingly and in line with e.g. EP2622073B1 (Vipergen), the after lysis step (iiiA) step of fusing (e.g. by ligating via use of a ligase) the nucleic acid molecules of the $B_{BoundTo}$T-structures with the bait bound to the prey of target may be performed according to steps (iv) to (vi) of claim 1 of EP2622073B1 (Vipergen)—i.e. by:

(A): applying the created $B_{BoundTo}$T-structures with the bait bound to the prey of target to an in vitro compartmentalization system—under binding conditions, which are conditions where a B-structure containing a binding entity capable of binding to a target molecule, binds more efficiently to the corresponding T-structure, than a B-structure containing a binding entity not capable of binding to the same target do—preferably, wherein the compartmentalization system comprises at least 2 times more individual compartments than the number of B-structures introduced in step (ii) under conditions wherein the B-structures, T-structures and $B_{BoundTo}$T-structures enter randomly into the individual compartments; and (B): fusing the nucleic acid molecules of a B-structure and a T-structure which are both present within the same individual compartment—which is fusing the nucleic acid molecule of the B-structure to the nucleic acid molecule of the T-structure—this structure is herein termed $BT_{Fused}$-structure and the $BT_{Fused}$-structure comprises the specific nucleic acid sequence information allowing to identify the binding entity and the specific nucleic acid sequence information allowing to identify the specific target; and (C): combining the content of the individual compartments of step (B) under conditions wherein there is no fusing of the nucleic acid molecules of a B-structure and a T-structure—wherein there is not created any new $BT_{Fused}$-structure not already created in step (B)—in order to get a library of $BT_{Fused}$-structures, wherein the library is an enriched library of species of $BT_{Fused}$-structures originating from binding pairs of target and binding entity when compared to $BT_{Fused}$-structures originating from nonbinding pairs of target and binding entity; and wherein the $B_{BoundTo}$T-structures remain suspended in solution in the individual compartments of step (A); and/or wherein the method does not rely on target immobilization on a solid support; and wherein the nucleic acid of $BT_{Fused}$-structures present in the enriched library of step (C) are amplified.

It may be preferred that step (iii) of the first aspect is step (iii)(B).

When step (iii) is step (iii)(B), the method as described herein may preferably a method, wherein the T-structure of (i) of first aspect comprises an enzyme fused to the target and this enzyme is due to the proximity created by the binding of the binding entity and target of the $B_{BoundTo}$T-structures of (ii) of first aspect capable of making an reaction on the B-structure of the $B_{BoundTo}$T-structure that marks B-structure and thereby makes it possible to distinguish the B-structure of the $B_{BoundTo}$T-structure from a B-structure that not have bound to target.

An example may e.g. be, wherein the enzyme fused to the target is a ligase and wherein there in step (ii) of first aspect is also introduced nucleic acid molecules that have complementary cohesive ends to the nucleic acid molecule of the B-structure and wherein the ligase due to the proximity ligates the introduced nucleic acid molecules to the nucleic acid molecule of the B-structure and thereby marks the B-structure.

Another example may e.g. be, wherein the enzyme fused to the target is an enzyme that due to the proximity is capable of using the nucleic acid molecule of the B-structure as a substrate to make a reaction and thereby marks the B-structure—an example could e.g. be an enzyme that could biotinylate the nucleic acid molecule.

Step (iv) of First Aspect

As discussed above, step (iv) reads:

"(iv): identifying, via use of the solution of (iii) and the nucleic acid molecules that comprises the specific nucleic acid sequence information allowing to identify the binding entity of the B-structures, at least one individual binding entity that binds within the cell of (ii) to at least one target of interest"

As understood by the skilled person—use of the specific nucleic acid sequence information allowing to identify the binding entity will preferably require some kind of sequencing.

It is or course routine work for the skilled person to sequence a nucleic acid molecule of interest.

Step (iv) may be made by based on prior art know techniques as e.g. discussed herein.

As understood by the skilled person and discussed herein—whether one uses option step (iii)(A) or step (iii)(B) may be seen as relating to how one prefers to make the identifying step (iv).

The "identifying" step (iv) of the first aspect preferably comprises a step, wherein the nucleic acid molecules that comprises the specific nucleic acid sequence information allowing to identify the binding entity of the B-structures are amplified.

The skilled person in the art can routinely identify numerous different strategies in order to amplify the nucleic acid in the fused genotypes, for example without being limited: PCR (U.S. Pat. No. 4,683,202; Mullis), Emulsion PCR (Nakano et al., J Biotechnol. 2003; 102(2):117-24), Digital PCR (Vogelstein, B; Kinzler K W (1999). "Digital PCR". Proc Natl Acad Sci USA. 96 (16): 9236-41), NASBA (Compton J. Nucleic acid sequence-based amplification. Nature. 1991; 350(6313):91-2), or Rolling Circle Amplification (American Journal of Pathology. 2001; 159:63-69)

Preferably, the nucleic acid molecules are amplified via PCR.

It may be preferred that there in the identifying step (iv) are identified at least two (such as e.g. at least 3 or at least 6 or at least 10) different individual binding entities that binds within the cell of (ii) to at least one target of interest.

In working example herein (see below) was there in the identifying step (iv) identified around 10 different individual binding entities.

It is evident that in order to be able to identify e.g. at least 10 different individual binding entities in this step (iv)—it is required that:
  the solution of step (iii)(A) comprises more than 10 different $B_{BoundTo}$T-structures; or
  the solution of step (iii)(B) comprises more than 10 different "binder marked B-structures".

EXAMPLES

Example 1

In-Cell Screening and Comparative In Vitro (i.e. not within a Cell) Screening of p38 Against a YoctoReactor Library Containing Approx. $10^8$ Different Binding Entities For overview see FIGS. 1 and 2.

Methods
DNA Oligonucleotides Used

```
vib7460
                                    (SEQ ID NO: 1)
AAAGCTGGGAGACACCA*A*T*G (* = phosphorothioated DNA bases)

vib7461
                                    (SEQ ID NO: 2)
T*T*G*GTGTCTCCCAGCTTTGA (* = phosphorothioated DNA bases)

vip7442
                                    (SEQ ID NO: 3)
A*G*C*ACTAAGCCTTGATGGCCACATTCCTA

CTTCTCCCTAAGGTGCAGTTTTGCCAAGG (* = phosphorothioated DNA bases)

vip7463
                                    (SEQ ID NO: 4)
xCCTTGGCAAAACTGCACCTTAGGGAGAAGTA

GGAATGTGGCCATCAAGGCTTAGTGC*T*C*A (x = 5'-aminomodifier C6;

* = phosphorothioated DNA bases)
```

Preparation of YoctoReactor Library (Lib027b_TA01)

The YoctoReactor library was constructed in a trimer format essentially as described elsewhere (Hansen et al. J. Am. Chem. Soc., 2009, 131 (3), pp 1322-1327) with the following modification: a 20-mer adapter nucleic acid molecule (consisting of oligonucleotides vip7460 (SEQ ID NO:1) and vip7461 (SEQ ID NO:2)) was ligated onto the YoctoReactor library thereby generating an adapter modified library, i.e. Lib027b_TA01. The constructed YoctoReactor DNA has an overlapping region (2 nucleotide 3'-overhang) which is complementary to the overlapping region (2 nucleotide 3'-overhang) on the target DNA.

Materials
Proprietary Vipergen YoctoReactor library (batch Lib027b, approx. $1.1*10^8$ different molecules) Oligonucleotides vip7460 (SEQ ID NO:1) and vip7461 (SEQ ID NO; 2) (100 µM stock prepared; Eurofins Genomics)
NaCl (4M stock prepared; Sigma-Aldrich)
HEPES, pH 7.5 (1M; Sigma-Aldrich)
Tris-HCl, pH 7.5 (1M; Sigma-Aldrich)
Glycogen (20 mg/mL; Thermo Fisher Scientific)
Ethanol (96%; Honeywell)
$MgCl_2$ (2M; Sigma-Aldrich)
PEG4000 (50%; Thermo Fisher Scientific)
ATP (100 mM stock prepared; Sigma-Aldrich)
T4 DNA ligase (30 Weiss U/µl; Thermo Fisher Scientific)
Water (molecular biology grade; Sigma-Aldrich)
20% TBE-PAGE gels (Kem-En-Tec)
NucleoSpin Gel and PCR Clean-up columns (Macherey-Nagel)
Qubit dsDNA HS Assay Kit (Thermo Fisher Scientific)
Quant-iT PicoGreen dsDNA Assay Kit (Thermo Fisher Scientific)

Protocol
The 20-mer nucleic acid adapter molecule was prepared by annealing vip7460 (SEQ ID NO: 1) and vip7461(SEQ ID NO:2) according to a published protocol (https://eu.idtdna.com/pages/education/decoded/article/annealing-oligonucleotides). The annealed oligos were precipitated by addition of 20 µl 4M NaCl, 1 µl glycogen and 1 ml ice-cold ethanol to a 300 µl annealing reaction and centrifugation (20,000 g at 4° C. for at least 30 min). The pellet was washed twice with 80% ethanol, air-dried at room temperature and dissolved in water to a concentration of 100 µM. The concentration was confirmed by Qubit assay (according to manufacturer's protocol) and the integrity of the 20-mer nucleic acid adapter was verified on 20% TBE-PAGE (200V, 55 min, 20° C.).

The 20-mer nucleic acid adapter was ligated to a proprietary YoctoReactor library (batch Lib027b) by mixing the YoctoReactor library (Lib027b) and the annealed adapter (2-fold molar excess) in a total of 200 µL water followed by addition of 200 µL 2× ligation master mix (80 mM Tris-HCl pH 7.5, 20 mM $MgCl_2$, 4% PEG4000, 2 mM ATP and 60U T4 DNA ligase). The ligation was allowed to proceed overnight at room temperature. The ligated YoctoReactor library was precipitated by adding 1.2 mL ice-cold ethanol, 1 µL glycogen and 40 µL 4M NaCl. The mixture was stored 1h at −20° C. before being pelleted by centrifugation (20, 000 g at 4° C. for at least 30 min) and air-dried at room temperature. To eliminate excess of the 20-mer nucleic acid adapter, the ligated YoctoReactor library was purified on NucleoSpin Gel and PCR Clean-up columns. The purified adapter modified YoctoReactor library was precipitated (NaCl, glycogen, and ice-cold ethanol) and dissolved in buffer (5 mM Tris-HCl pH 7.5, 20 mM NaCl, 0.001% Tween20) at a concentration of 47.9 µM (determined by PicoGreen Assay according to manufacturer's protocol). Importantly, the adapter modified YoctoReactor library (i.e. Lib027b_TA01) was 100% competent in ligation to vip7442 (SEQ ID NO:3)/vip7463 (SEQ ID NO:4) target DNA.

Preparation of CAIX-Binder (i.e. Bait=VD11-4-2) Attached to Target DNA (TD_VD11-4-2)

The small molecule CAIX-binder, VD11-4-2, was covalently attached to a 60-mer oligonucleotide (vip7463). The oligonucleotide was hereafter assembled with a reverse complementary oligonucleotide (vip7442 (SEQ ID NO; 3)), forming a double stranded nucleic acid molecule (i.e. target DNA) attached to the bait compound, VD11-4-2. The constructed target DNA (i.e. TD_VD11-4-2) has an overlapping region (2 nucleotide 3'-overhang) which is complementary to the overlapping region (2 nucleotide 3'-overhang) on the YoctoReactor DNA.

Materials
Pentafluorophenylsulfonamide (Fluorochem, 034664)
8-Mercaptooctanoic acid (Sigma-Aldrich, 675075)
Anhydrous methanol (Fisher Scientific, 10499560; stored over 4Å MS)
Triethylamine (Sigma-Aldrich, 90340)
Hydrogen peroxide solution (Sigma-Aldrich, 95321)
Cyclooctyl amine (Sigma-Aldrich, C110604)
HPLC grade water (Fisher Scientific, 10221712)
Triethylammonium acetate (Sigma-Aldrich, 90358)
Acetonitrile (Fisher Scientific, 10629112)
DMSO (Sigma-Aldrich, D8418)
Ethyl-(N',N'-dimethylamino)propylcarbodiimide hydrochloride (EDC; Sigma-Aldrich, E6383)
N-hydroxysuccinimide (NHS; Sigma-Aldrich, 130672)
N-Methylpyrrolidone (NMP; Sigma-Aldrich, 494496)

Protocol

An analogue of VD11-4-2 was prepared using an adapted procedure from V. Dudutiene et al. ("Discovery and Characterization of Novel Selective Inhibitors of Carbonic Anhydrase IX"; J. Med. Chem. 2014, 57, 9435-9446). Instead of 2-mercaptoethanol, 8-mercaptooctanoic acid was used, and an analogue carrying a distal carboxylic acid was produced:

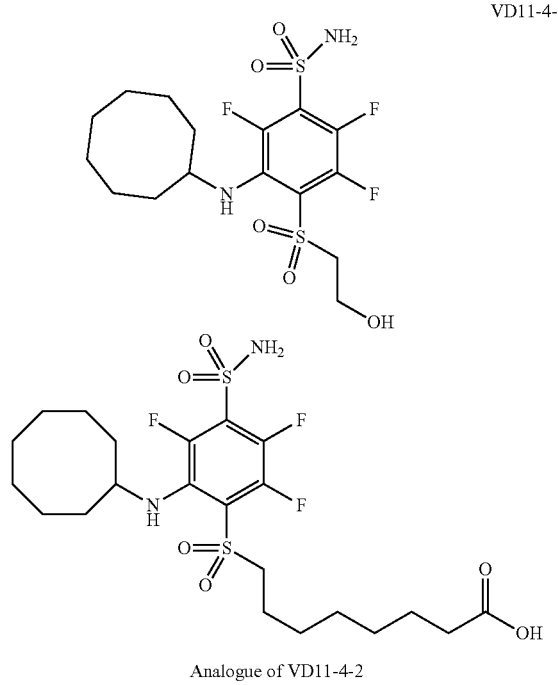

VD11-4-2

Analogue of VD11-4-2

The HPLC purified product (3.3 mg) was subsequently activated using ethyl-(N',N'-dimethylamino)propylcarbodiimide hydrochloride (EDC, 1.2 mg) and N-hydroxysuccinimide (NHS, 0.7 mg) in N-methylpyrrolidine (NMP, 60 μL). The crude activation mixture (50 μL) was added to a premixed solution of vip7463 (SEQ ID NO:4) (10 nmol; 100 μL of 100 μM), HEPBS buffer (100 μL, 1 M stock), NMP (200 μL) and water (50 μL).

After coupling for 16h, the DNA was EtOH precipitated and the crude conjugate purified by RP-HPLC using triethylammonium acetate in water/MeCN. Fractions with desired conjugate were concentrated by lyophilization and final product dissolved in water. QC by LCMS (ESI; neg mode): obs m/z 19322, calc 19324.6.

The purified single-stranded conjugate, i.e. vip7463 (SEQ ID NO:4)_VD11-4-2, was subsequently hybridized to the reverse complementary DNA oligonucleotide vip7442 (SEQ ID NO:3), hereby generating double stranded target DNA attached to VD11-4-2 (i.e. TD_VD11-4-2).

In Vitro Screening on p38 Conjugated to DNA Outside Oocytes (e1; Reference)

An in vitro screening (i.e. not within a cell) on recombinant p38 protein conjugated to DNA against Lib027b_TA01 (i.e. the same YoctoReactor library applied for in-cell screenings) was performed for reference. Conjugation of p38 protein to target DNA, and subsequent screening against Lib027b_TA01 (20 nM p38 conjugated to target DNA was screened against approx. $5.6*10^{12}$ library molecules per μl) was performed essentially as described previously (Petersen et al., "Novel p38α MAP kinase inhibitors identified from YoctoReactor DNA-encoded small molecule library", Med. Chem. Commun., 2016, 7, 1332-1339).

In-Cell Screening on p38 Expressed in Oocytes (e2 and e3)
Expression of Target-Prey Fusion Protein (e.g., CAIX-p38) in *Xenopus laevis* Oocytes A gene encoding p38 (Uniports accession code: Q16539) N-terminally fused via a 6-amino acid linker to the catalytic domain of human CAIX was synthesized and sub-cloned between the HindIII and BamHI sites in the pSP64 expression vector (Eurofins Genomics). The vector was linearized with EcoRI, and mRNA was synthesized with the Ambion mMESSAGE mMACHINE SP6 transcription kit (Thermo Fisher Scientific). mRNA was purified via RNeasy columns (Qiagen). Approx. 50 ng of CAIX-p38 mRNA was injected in a volume of 50 nL (diluted in water) into *Xenopus laevis* oocytes (Ecocyte Bioscience) using a Nanoliter 2010 injector (World Precision Instruments). The oocytes were maintained at 18° C. in Modified Barth's Medium (in mM, 88 NaCl, 1 KCl, 0.4 $CaCl_2$, 0.33 $Ca(NO_3)_2$, 0.8 $MgSO_4$, 5 Tris-HCl, 2.4 $NaHCO_3$, pH 7.4) until experiments.

Quantification of Expressed Target-Prey Fusion Protein (e.g., CAIX-p38) in *Xenopus laevis* Oocytes Four days after injection of mRNA, expression of CAIX-p38 protein inside *Xenopus laevis* oocytes was quantified by using a human CAIX DuoSet ELISA assay (Bio-techne). As control, uninjected *Xenopus laevis* oocytes were processed in parallel. Briefly, one *Xenopus laevis* oocyte was crushed in 25 μl buffer (1 mM EDTA, 0.5% Triton X-100, 5 mM NaF in PBS) by centrifugation (20,000 g for 2 min at 4° C.), supernatant was transferred to an ELISA plate coated with CAIX-capture antibody and incubated for 1h at RT. All wells were washed (three times in wash buffer; 0.05% Tween20 in PBS), and biotinylated CAIX-detection antibody was added. The plate was incubated for 1h at RT, and all wells were washed. Streptavidin conjugated to horseradish peroxidase (streptavidin-HRP) was added, and the plate was incubated for 20 min at RT in the dark. All wells were washed before addition of the HRP substrate TMB SENS (Kem-En-Tec). The plate was incubated for 5 min at RT in the dark before the reaction was stopped by addition of 2M $H_2SO_4$. The optical density at 450 nm was determined on a DTX880 Multimode Detector (Beckman Coulter). Based on a CAIX standard curve, which was generated in parallel with recombinant CAIX protein, the concentration of CAIX-p38 protein expressed inside *Xenopus laevis* oocytes was determined to be approx. 200 nM.

Introduction of Target DNA and YoctoReactor Library into *Xenopus laevis* Oocytes A diverse YoctoReactor library (Lib027b_TA01) consisting of approx. $1.1*10^8$ different molecules (i.e., potential binders coupled to double stranded nucleic acid molecule) was mixed with TD_VD11-4-2 (i.e., target DNA covalently attached to bait compound, VD11-4-2), and the mixture was injected into *Xenopus laevis* oocytes expressing CAIX-p38 protein. Injection of YoctoReactor library and TD_VD11-4-2 was done 4 days after injection of mRNA encoding CAIX-p38. A total of 50 nL, consisting of a total of approx. $6.6*10^{11}$ YoctoReactor library molecules and $1.5*10^{11}$ TD_VD11-4-2 molecules, was injected into each oocyte (e2). In parallel experiments, the Lib027b_TA01/TD_VD11-4-2 mix was supplemented with 0.1 µg/ml RNaseA before injections (e3). Injection of RNaseA was done to digest endogenous RNA that could potentially affect the selection process inside the oocytes.

The *Xenopus laevis* oocytes were incubated at 18° C. for 2-4h. Within this period, the expressed CAIX-p38 protein was allowed to bind to: 1) YoctoReactor library ligands (binding to the protein of interest, p38), and 2) TD_VD11-4-2 (binding to CAIX-tag).

Breaking of *Xenopus laevis* Oocyte Membrane and DNA Ligation

The membrane of the *Xenopus laevis* oocyte was broken in order to release the binding complexes from the cell, i.e., CAIX-p38 bound to: 1) YoctoReactor library ligands and 2) TD_VD11-4-2. The DNA fragments associated to the CAIX-p38 protein (i.e. target DNA and YoctoReactor DNA, respectively) have overlapping regions resulting in the potential assembly of the two fragments to combined fragments by DNA ligation. The ligation will be driven by proximity when both DNA fragments are associated to the CAIX-p38 protein, thus creating an enriched library with a higher fraction of members having the desired binding activity.

For breaking of the *Xenopus laevis* oocyte membrane, one oocyte was centrifuged (20,000 g for 2 min at 4° C.) in 600 µl ligation buffer without ATP and ligase. The supernatant (600 µl) was diluted in two sequential steps into a total of 11 mL ligation buffer (50 mM Tris-HCl, 50 mM NaCl, 0.1% Triton X-100, 0.75% BSA, 9 mM KCl, 4.5% glycerol, 1 mM DTT, 5 mM $MgCl_2$, 1 mM ATP, pH 7.4) supplemented with 300 Weiss units T4 DNA ligase (Thermo Fisher Scientific). The binding complex was thereby diluted approx. $10^4$-fold in total, and ligation was allowed to proceed for 4 min at 16° C. Then, T4 DNA ligase was inactivated by addition of 11 mL stop buffer (NTI buffer supplemented with 50 mM EDTA, 0.2 µg/µl Proteinase K, 0.2% N-lauryl sarcosine) and the resulting mixture was subsequently incubated at 65° C. for 1h. After cooling to RT, DNA was purified on Nucleo-Spin Gel and PCR Clean-up columns (Macherey-Nagel).

Amplification of Ligated DNA

The ligated and purified DNA fragments were treated with Lambda Exonuclease (to remove free, unligated 5'-phosphorylated DNA fragments) and amplified by PCR.

PCR Mixture (Final Concentrations):
  25 µl purified ligated DNA (PCR template)
  1× Vent (-exo) PCR buffer (New England Biolabs)
  0.4 mM CleanAmp dNTP (tebu-bio)
  6 mM $MgCl_2$ (Sigma-Aldrich)
  3% DMSO (Sigma-Aldrich)
  0.25 µM forward PCR primer
  0.25 µM backward PCR primer
  1 U Vent (-exo) polymerase (New England Biolabs)
  Water to a total of 100 µl The mixture was subjected to thermal cycling by applying the following program in a PCR machine:
  95° C. 10 min, 27 cycles of (95° C. 30 sec, 62° C. 30 sec, 72° C. 2 min30 sec), 72° C. 2 min The resulting library of DNA fragments was purified on NucleoSpin Gel and PCR Clean-up columns (Macherey-Nagel), and subjected to a second round of PCR to introduce priming sites for Illumina sequencing.

PCR mixture:
  5 µl purified amplified DNA (PCR template)
  1× Vent (-exo) PCR buffer (New England Biolabs)
  0.2 mM dNTP (Thermo Fisher Scientific)
  6 mM $MgCl_2$ (Sigma-Aldrich)
  0.5M betaine (Sigma-Aldrich)
  0.25 µM forward Illumina primer
  0.25 µM backward Illumina primer
  1 U Vent (-exo) polymerase (New England Biolabs)
  Water to a total of 100 µl The mixture was subjected to thermal cycling by applying the following program in a PCR machine:
  92° C. 2 min, 10 cycles of (92° C. 30 sec, 62° C. 30 sec, 72° C. 2 min30 sec), 72° C. 2 min The resulting library of DNA fragments was purified by Agencourt AMPure XP (Beckman Coulter Life Sciences) and preparative 10% TBE-PAGE (Kem-En-Tec) and submitted for Illumina DNA sequencing (Fulgent Genetics).

Analysis of Enrichment by DNA Sequencing Using Illumina Sequencing Technology

DNA sequencing data was decoded and analyzed as described elsewhere (Petersen et al., "Novel p38α MAP kinase inhibitors identified from yoctoReactor DNA-encoded small molecule library", Med. Chem. Commun., 2016, 7, 1332-1339). By counting how many times a given library member was observed within a sequencing sample, hits that were enriched above the random ligation events could be identified. Library members observed many times are target binders (hits) whereas compounds observed only a few times are dominantly results of the random events (background). The number of observations based on random event represents a linear decay line on a logarithmic scale (red spheres in signal plot). Thus, library members with observation numbers above the transition from decay phase to signal phase are thus above the mathematical threshold (MT, green spheres in signal plot). From three individual selection experiments (e1-e3), signal plots were produced (panel A-C on FIG. 3 herein). Signal plot A originates from screening on p38 conjugated to target DNA against YoctoReactor library Lib027b_TA01 (e1, reference), and signal plots B or C are from in-cell screenings on p38 expressed in oocytes without (e2) or with co-injection of RNaseA (e3). From screening against approx. $1.1*10^8$ different molecules in e1-e3, we identified a total of 39 hits above MT (green spheres). The 39 hits were combined and annotated for number of observations in the three data pools from DNA sequencing (panel D on FIG. 3). The 39 hits were observed above MT in at least one of the three experiments. A significant number of hits were found in both the reference experiment (e1) and in the two in-cell screening experiments (e2 or e3). Hit ID #31 was a previously validated p38a inhibitor (vpc00249; $IC_{50}$ 0.51 µM; Petersen et al., "Novel p38α MAP kinase inhibitors identified from yoctoReactor DNA-encoded small molecule library", Med. Chem. Commun., 2016, 7, 1332-1339).

Conclusions

As discussed above, based on an in vitro display library of around $10^8$ different binding entities—in this "within the cell" screening example there was in the identifying step (corresponding to identifying step (iv) of the first aspect) identified around 10-30 different individual good binder chemical compound binding entities, including a previously validated p38 inhibitor together with several non-validated hits. In the present context this is considered an acceptable representative high number of good binder compounds of the library.

A reason for that the identified number of good binder entities are considered acceptable relates to that for this target (i.e. p38) was, as discussed above, a comparative in vitro (i.e. not within a cell) screening of the same in vitro display library was made and there was identified around 10 different individual good binders. The number of identified binders of the "within the cell" screening, was at least comparable to the comparative in vitro screening—i.e. it was considered acceptable.

Further, the individual good binders identified in the within the cell screening of the present invention corresponded to the good binders identified in the comparative in vitro screening.

If there for instance only would have been identified one or two individual good binder chemical compound binding entities in the "within the cell" screening of this example, then would it not have been considered as good as the around 10 different individual good binders actually identified in this example. One reason for this relates to that if only 1-2 individual good binders would have been identified, then there could maybe have been a risk of losing possible relevant good binders—i.e. loosing valuable good binder information.

As discussed, some the identified good binders of the "within a cell" and comparative in vitro screening were the same and some of the good binders of the "within a cell" screening were not identified in the comparative in vitro screening—a reason for this may relate to that some of the in "real life" good binders maybe could only be identified under the natural "within the cell" binding conditions (i.e. step (ii)(b) of the first aspect) of the "within the cell" screening method of this example—i.e. a method of the present invention.

Example 2

Comparative Example—Use of 3 Phosphorothioate Bonds have been Compared Against Unmodified DNA (i.e. Zero Phosphorothiate Bonds)

Methods
DNA Oligonucleotides Used (Schematic Illustration)
Double Stranded Nucleic Acid Molecules (i.e. Target DNA, TD) Injected into *Xenopus* leavis Oocytes:

TD_001
unmodified

TD_002
PS-bonds installed on upper strands

TD_003
PS-bonds installed on upper and lower strands

* = phosphorothioate bond (PS).

Note: TD_001, TD_002 and TD_003 contain a 2-nt overhang in 3-end of lower strand, which is complementary to the 2-nt overhang on ligation DNA (i.e. LD_001).

Double Stranded Nucleic Acid Ligation Molecule (i.e. Ligation DNA, LD):

LD_001
unmodified

Note: LD_001 contain a 2-nt overhang in 3-end of upper strand, which is complementary to the 2-nt overhang on target DNA (i.e TD_001, TD_002, TD_003).

Evaluation of Ligation Potential of Target DNA with or without Phosphorothioate Bonds after Injection into and Extraction from *Xenopus* Leavis Oocytes Target DNA with or without phosphorothioated DNA bases (i.e. TD_001, TD_002 and TD_003) was injected into *Xenopus* leavis oocytes. The target DNA was incubated inside oocytes for increasing time intervals before the membrane of the *Xenopus* leavis oocyte was broken and the injected target DNA was recovered. The ligation potential of the recovered target DNA was examined in a DNA ligation reaction with ligation DNA (i.e. LD_001). Note, retaining the ligation potential of target DNA after incubation inside a cell is a critical parameter in the present context of in-cell screenings.

Injection of Target DNA into *Xenopus* Leavis Oocytes

Approx. 1-2 pmol of target DNA with or without phosphorothioate bonds (i.e. TD_001, TD_002 or TD_003) was injected in a volume of 50 nL (diluted in water) into *Xenopus* leavis oocytes (Ecocyte Bioscience) using a Nanoliter 2010 injector (World Precision Instruments). The oocytes were maintained at 18° C. in Modified Barth's Medium (in mM, 88 NaCl, 1 KCl, 0.4 $CaCl_2$), 0.33 $Ca(NO_3)_2$, 0.8 $MgSO_4$, 5 Tris-HCl, 2.4 $NaHCO_3$, pH 7.4). The oocytes were incubated for increasing time intervals before the membrane was broken and the injected target DNA was recovered (as detailed below).

Breaking of *Xenopus* Leavis Oocyte Membrane and Recovery of Injected Target DNA The membrane of the *Xenopus* leavis oocyte was broken in order to recover the injected target DNA. For breaking of the *Xenopus* leavis oocyte membrane, five oocytes were centrifuged (20,000 g for 2 min at 4° C.) in 200 µl crushing buffer (10 mM Tris-HCl, 150 mM NaCl, 0.01% Tween-20). The recovered target DNA (originating from five oocytes) was purified on NucleoSpin Gel and PCR Clean-up columns. The purified target DNA was precipitated (NaCl, glycogen, and ice-cold ethanol) and pelleted by centrifugation (20,000 g at 4° C. for at least 30 min). The DNA pellet was air-dried at room temperature and dissolved in water.

DNA ligation

The ligation potential of the recovered target DNA was evaluated by applying it in a DNA ligation reaction together with ligation DNA, i.e. LD_01. The purified target DNA (originating from five oocytes) was mixed with approx. 2 pmol of LD_01 ligation DNA in ligation buffer (50 mM Tris-HCl, 50 mM NaCl, 0.1% Triton X-100, 0.75% BSA, 9 mM KCl, 4.5% glycerol, 2 mM DTT, 10 mM $MgCl_2$, 2 mM ATP, pH 7.4) supplemented with approx. 1 Weiss units T4 DNA ligase (Thermo Fisher Scientific). The ligation reaction was allowed to proceed for 1-2h at 16° C. The ligation mixture was applied to native PAGE (10% TBE-PAGE, 200V, 35 min, room temperature) to allow for evaluation of the ligation potential of the recovered target DNA. The ligation potential of unmodified target DNA (i.e. TD_001) was lost after incubation inside a *Xenopus* leavis oocyte in a time-dependent manner. Specifically, 50% of ligation potential was lost after incubation for 30 min and ligation potential was almost completely lost after incubation for 1h inside the oocyte. For target DNA with phosphorothioate bonds installed in one strand (i.e. TD_002), approx. 50% of the ligation potential was lost after incubation for 2h inside the oocyte. In contrast, when phosphorothioate bonds were installed in both strands of the target DNA (i.e. TD_003), the ligation potential was almost not affected after incubation for 2h inside the oocyte.

Conclusions

The results of this example demonstrate that use of 3 phosphorothioate bonds gives surprising significant technical advantages in the present context as compared to use of unmodified DNA (i.e. zero phosphorothiate bonds).

REFERENCE LIST

1: EP1809743B1 (Vipergen)
2: EP1402024B1 (Nuevolution)
3: EP1423400B1 (David Liu)
4: Nature Chem. Biol. (2009), 5:647-654 (Clark)
5: WO 00/23458 (Harbury)
6: Nature Methods (2006), 3(7), 561-570 7: 2006 (Miller)
7: Nat. Biotechnol. 2004; 22, 568-574 (Melkko)
8: Nature. (1990); 346(6287), 818-822 (Ellington)
9: Proc Natl Acad Sci USA (1997). 94 (23): 12297-302 (Roberts)
10: WO2006/053571A2 (Rasmussen)
11: EP2622073B1 (Vipergen)
12: Lynn M M et al. ("Identification of Ligand-Target Pairs from Combined Libraries of Small Molecules and Unpurified Protein Targets in Cell Lysates"; J. Am. Chem. Soc. 2014, 136, 3264-3270)
13: Zining Wu et al. ("Cell-Based Selection Expands the Utility of DNA-Encoded Small-Molecule Library Technology to Cell Surface Drug Targets . . . "; ACS Comb. Sci. 2015, 17, 722-731)
14: M. Schurmann et al. ("Small-Molecule Target Engagement in Cells"; Cell Chemical Biology 23, Apr. 21, 2016)
15: Ron Milo ("What is the total number of protein molecules per cell volume? . . . "; Bioessays 35: 1050-1055, 2013)
16: V. Dudutiene et al. ("Discovery and Characterization of Novel Selective Inhibitors of Carbonic Anhydrase IX"; J. Med. Chem. 2014, 57, 9435-9446)
17: Petersen et al. ("Novel p38α MAP kinase inhibitors identified from yoctoReactor DNA-encoded small molecule library", Med. Chem. Commun., 2016, 7, 1332-1339)

The invention claimed is:

1. A method for screening of an in vitro display library for binding within a cell of a small-molecule chemical compound binding entity of the library to a protein or RNA target of interest in order to identify at least one individual chemical compound binding entity of the library that is capable of binding within the cell to the protein or RNA target of interest and wherein the method comprises the steps of:
   (i): expressing at least one target $T^n$, wherein n=1 or more, in a cell and wherein the at least one target is a protein or RNA—the structure of the target is herein termed T-structure;
   (ii): introducing an in vitro display library into the cell of (i), wherein:
   (a): the library is a library of at least 1000 different binding entities B., wherein n=1000 or more, wherein each binding entity is attached to a nucleic acid molecule and the nucleic acid molecule comprises specific nucleic acid sequence information allowing to identify the binding entity—wherein once one knows the specific nucleic acid sequence information of the nucleic acid molecule one directly knows the structure of the specific binding entity attached to the nucleic acid molecule and wherein the binding entities of the library are chemical compounds with an average molecular weight MW below 10000 dalton—the structure of the binding entity attached to the nucleic acid molecule is herein termed B-structure; and
   (b): the library is introduced into the cell under binding conditions, which are conditions where a B-structure containing a binding entity capable of binding to a target molecule, binds more efficiently to the corresponding T-structure, than a B-structure containing a binding entity not capable of binding to the same target do and wherein one within the cell gets binding of at least one of the binding entities to at least one target thereby creating within the cell a complex comprising a B-structure bound to a T-structure, which is termed $B_{BoundTo}$T-structure;
   (iii): making lysis of the cell of (ii) to breaking down the membrane of cells in order to:
   (A): get the $B_{BoundTo}$T-structures of (ii) out of the cell and thereby obtain a solution comprising $B_{BoundTo}$T-structures, wherein the $B_{BoundTo}$T-structures are not within the cells; or
   (B): get B-structures out of the cells that had bound to target in step (ii) and have been marked before step (iii) in a way that makes it possible to distinguish the marked B-structures from a B-structure that has not bound to target in step (ii) and thereby obtain a solution comprising binder marked B-structures, wherein the binder marked B-structures are not within the cells; and
   (iv): identifying, via use of the solution of (iii) and the nucleic acid molecules that comprises the specific nucleic acid sequence information allowing to identify the binding entity of the B-structures, at least one individual binding entity that binds within the cell of (ii) to at least one target of interest.

2. The method of claim 1, wherein the target T is a protein and wherein the cell is a eukaryotic cell.

3. The method of claim 1, wherein the cell is a *Xenopus* oocyte.

4. The method of claim 3, wherein the cell is a *Xenopus laevis* oocyte.

5. The method of claim 3, wherein the introducing of the in vitro display library into the cell of step (ii) of claim 1 is done via injection of the in vitro display library into the *Xenopus* oocyte; and
   wherein the in vitro display library of step (ii) of claim 1 is a library of at least $10^6$ different binding entities $B_n$, wherein $n=10^6$.

6. The method of claim 1, wherein the concentration of T-structures in the binding step step (ii)(b) of claim 1 is at least $10^{-10}$ M.

7. The method of claim 1, wherein the step (iii) of claim 1 is step (iii)(A).

8. The method of claim 7, wherein step (iv) of claim 1 is done by:
   binding $B_{BoundTo}$T-structures of the solution (iii)(A) of to a solid support via binding of target of the $B_{BoundTo}$T-structures to the solid support and remove B-structures not bound to target and thereby not bound to the solid support; and p1 identifying, via use of the specific nucleic acid sequence information allowing to identify the binding entity of the $B_{BoundTo}$T-structures bound to the solid support, at least one individual binding entity that binds within the cell of (ii) to at least one target of interest.

9. The method of claim 7, wherein:
   the T-structure of (i) of claim 1 comprises a prey, which is a target-prey fusion protein, and there in
   step (ii) of claim 1 is also introduced a bait attached to a nucleic acid molecule and the nucleic acid molecule comprises specific nucleic acid sequence information allowing to identify the specific target and wherein the bait binds to the prey of the target in step (ii) of claim 1 and thereby creates $B_{BoundTo}$T-structures with the bait bound to the prey of target;
   after lysis step (iii)(A)—fusing the nucleic acid molecules of the $_{BoundTo}$T-structures with the bait bound to the prey of target, wherein the fused nucleic acid molecules comprise the sequence information allowing to identify binding entity and target; and identifying in step (iv) of claim 1 via use of the specific nucleic acid sequence information allowing to identify the binding entity and target of the fused nucleic acid molecules of the preceding step at least one individual binding entity that binds within the cell of (ii) to at least one target of interest.

10. The method of claim 9, wherein the cell is a *Xenopus* oocyte.

11. The method of claim 9, wherein before the "fusing the nucleic acid molecules of the $B_{BoundTo}$T-structures with the bait bound to the prey of target" step is made there is a dilution step of the solution obtained from cell lysis step (iii) and wherein the dilution is a diluting the solution of at least $10^2$ fold;

and— wherein there is only one target (n=1) in step (i) of claim 1; and wherein the "identifying" step (iv) comprises a step, wherein the fused nucleic acid molecules that comprise the sequence information for binding entity and for target are amplified; and wherein the "prey-bait" system is:
   prey: tetrameric streptavidin and bait: biotin;
   prey: monomeric streptavidin and bait: biotin;
   prey: His-tag and bait: NTA;
   prey: 20 kDa protein tag mutant of the DNA repair protein $\Omega^6$-alkylguanine DNA alkyltransferase and bait: benzyl guanine (BG);
   prey: 34 kDa monomeric protein tag modified from a bacteria dehalogenase and bait: reactive chloroalkane linker bound to a functional group;
   prey: carbonic anhydraseIX (CAIX) and bait: VD11-4-2; or
   prey: maltose binding protein (MBP) and bait: maltose or maltotriose; and wherein the nucleic acid molecule attached to the bait is DNA and the nucleic acid molecule of the B-structure is DNA.

12. The method of claim 9, wherein the nucleic acid molecule attached to the bait is a nucleic acid molecule which has complementary cohesive ends to the nucleic acid molecule of the B-structure; and wherein there are phosphorothioate bonds installed in the phosphate backbone at the complementary cohesive ends of the nucleic acid molecule of the B-structure and the nucleic acid molecule attached to the bait; and the number of phosphorothioate bonds is for each nucleic acid molecule at least 2 phosphorothioate bonds.

13. The method of claim 1, wherein the step (iii) of claim 1 is step (iii)(B);

and wherein method is a method, wherein
   the T-structure of (i) of claim 1 comprises an enzyme fused to the target and this enzyme is due to the proximity created by the binding of the binding entity and target of the $B_{BoundTo}$T-structures of (ii) of claim 1 capable of making an reaction on the B-structure of the $B_{BoundTo}$T-structure that marks B-structure and thereby makes it possible to distinguish the B-structure of the $B_{BoundTo}$T-structure from a B-structure that not have bound to target; and wherein the enzyme fused to the target is a ligase and wherein there in step (ii) of first aspect is also introduced nucleic acid molecules that have complementary cohesive ends to the nucleic acid molecule of the B-structure and wherein the ligase due to the proximity ligates the introduced nucleic acid molecules to the nucleic acid molecule of the B-structure and thereby marks the B-structure.

14. The method of claim 1, wherein the "identifying" step (iv) comprises a step, wherein the nucleic acid molecules that comprises the specific nucleic acid sequence information allowing to identify the binding entity of the B-structures are amplified.

15. The method of claim 1, wherein there in the identifying step (iv) are identified at least 6 different individual binding entities that binds within the cell of (ii) to at least one target of interest; and wherein there is only one target (n=1) in step (i).

16. The method of claim 11, wherein the prey-bait system is prey:
   carbonic anhydraseIX (CAIX) and bait: VD11-4-2.

17. The method of claim 9, wherein the cell is a *Xenopus laevis* oocyte.

18. The method of claim 11, wherein the fused nucleic acid molecules that comprise the sequence information for binding entity and for target are amplified by use of polymerase chain reaction (PCR).

19. The method of claim 14, wherein the nucleic acid molecules are amplified by use of polymerase chain reaction (PCR).

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aaagctggga gacaccaatg                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ttggtgtctc ccagctttga                                                    20

<210> SEQ ID NO 3
<211> LENGTH: 58
<212> TYPE: DNA
<213> ORGANISM: Artificial Sequence
<220> FEATURE:
<223> OTHER INFORMATION: Primer
```

```
<400> SEQUENCE: 3
agcactaagc cttgatggcc acattcctac ttctccctaa ggtgcagttt tgccaagg        58

<210> SEQ ID NO 4
<211> LENGTH: 60
<212> TYPE: DNA
<213> ORGANISM: Artificial Sequence
<220> FEATURE:
<223> OTHER INFORMATION: Primer

<400> SEQUENCE: 4
ccttggcaaa actgcacctt agggagaagt aggaatgtgg ccatcaaggc ttagtgctca      60
```